United States Patent
Staples et al.

(10) Patent No.: US 6,171,801 B1
(45) Date of Patent: *Jan. 9, 2001

(54) METHODS FOR RELEASING A LIGAND FROM A COMPLEX

(75) Inventors: Mark A. Staples, San Jose; Carolyn J. Haley, Morgan Hill; Richard F. Parrish, San Jose; Wesley W. Zmolek, Freemont, all of CA (US)

(73) Assignee: Dade Behring Marburg GmbH, Marburg (DE)

( * ) Notice: Under 35 U.S.C. 154(b), the term of this patent shall be extended for 0 days.

This patent is subject to a terminal disclaimer.

(21) Appl. No.: 08/896,244

(22) Filed: Jul. 17, 1997

Related U.S. Application Data

(60) Provisional application No. 60/022,133, filed on Jul. 18, 1996.

(51) Int. Cl.$^7$ ........................ G01N 33/53; G01N 33/531; G01N 1/18; G01N 1/00
(52) U.S. Cl. ........................ 435/7.1; 435/7.9; 435/961; 435/962; 436/177; 436/174; 436/536; 436/825
(58) Field of Search ................ 435/7.9, 7.1, 962, 435/961; 436/501, 174, 825, 177, 536

(56) References Cited

U.S. PATENT DOCUMENTS

| | | |
|---|---|---|
| 3,817,837 | 6/1974 | Rubenstein et al. ............... 195/103.5 |
| 3,996,345 | 12/1976 | Ullman et al. ............... 424/12 |
| 4,052,504 | 10/1977 | Hertl et al. ............... 424/1 |
| 4,110,076 | 8/1978 | Margherita ............... 23/230.6 |
| 4,233,402 | 11/1980 | Maggio et al. ............... 435/7 |
| 4,275,149 | 6/1981 | Litman et al. ............... 435/7 |
| 4,318,980 | 3/1982 | Boguslaski et al. ............... 435/7 |
| 4,454,232 | 6/1984 | Breglio et al. ............... 436/504 |
| 4,486,530 | 12/1984 | David et al. ............... 435/7 |
| 4,857,453 | 8/1989 | Ullman et al. ............... 435/7 |
| 4,868,104 | 9/1989 | Kurn et al. ............... 435/6 |
| 4,959,303 | 9/1990 | Milburn et al. ............... 435/7 |
| 5,089,390 | 2/1992 | Davalian et al. ............... 435/7.93 |
| 5,185,243 | 2/1993 | Ullman et al. ............... 435/6 |

FOREIGN PATENT DOCUMENTS

| | | |
|---|---|---|
| 2014233 | 10/1990 | (CA) . |
| 0 100 543 | 2/1984 | (EP) . |
| 0 155 104 | 9/1985 | (EP) . |
| 0 165 669 | 12/1985 | (EP) . |
| 0 218 309 | 4/1987 | (EP) . |
| 0 392 332 | 10/1990 | (EP) . |
| WO 83/00147 | 1/1983 | (WO) . |
| WO 96/02004 | 1/1996 | (WO) . |

OTHER PUBLICATIONS

Bowmer et al. J. Pharm. Pharmacol. 37: 812–815, 1985.*
Nishjio et al. Chem. Pharm. Bull. 33: 2648–2653, 1985.*
Broughton and Strong, *Clin. Chem.* 22:726–732 (1976).
Butler, *J. Immunol. Meth.* 7:1–24 (1975).
Carey, "Organic Chemistry," McGraw Hill Inc., New York, New York, First edition, 1987, pp. 994–995 and 609.
Cuatrecasas, *J. Biol. Chem,* 245:3059 (1970).
Epinette, et al., *Journal of the American Academy of Dermatology* 17(6):962–71 (1987).
Galfre, et al., (1981) Preparation of monoclonal antibodies: strategies and procedures, *Methods Enzymol.* 73:3–46.
Grabarek, et al., (1990) Zero–length crosslinking procedure with the use of active esters, *Anal. Biochem.* 185:131–135.
Heathcock, et al., "Introduction to Organic Chemistry," MacMillan Publishing Company, New York, New York, Third edition, 1985, pages 814 and 493.
Köhler and Milstein, *Nature* 256:495–497, 1975.
Langman, et al., *Therapeutic Drug Monitoring* (1994) 16:602–607.
Lee, et al., *Pharmaceutical Research* 7(2):161–166 (1990).
Lymphocyte Hybridomas, ed. Melchers, et al. Springer–Verlag (New York 1978).
*Nature* 266:495 (1977).
Nelson, et al., *Journal of Medicinal Chemistry* 33(2):833–838 (1990).
Nerli, et al., *Arch Int Physiol Biochim Biophys* (1994) 102(1):5–8.
Playfair, et al., *Br. Med. Bull.* 30:24–31 (1974).
*Science* 208:693 (1980).
Seth, et al., *Clin Chem* (1975) 21(10):1406–1413.
Shaw, et al., *Therapeutic Drug Monitoring* (1995) 17:690–699.
Wu, *Perspectives in Drug Discovery and Design* (1994) 2:185–204.
Yalow, et al., *J. Clin. Invest.* 39:1157 (1960).

(List continued on next page.)

*Primary Examiner*—James C. Housel
*Assistant Examiner*—S. Devi
(74) *Attorney, Agent, or Firm*—Cara Z. Lowen

(57) ABSTRACT

One aspect of the present invention relates to a method for releasing a ligand from a complex thereof. The method comprises contacting a medium suspected of containing such complex with an effective amount of a compound effective in releasing the ligand. Another aspect of the present invention is an improvement in a method for the determination of an analyte that is a member of a specific binding pair in a sample suspected of containing such analyte. The method comprises the steps of (a) providing in an assay medium the sample and a binding partner for the analyte and (b) detecting the binding of the binding partner to the analyte. The improvement comprises including in the assay medium a compound of the invention in an amount sufficient to enhance the accuracy of the determination. The invention has particular application to a method for releasing mycophenolic acid from a complex thereof. The method provides an improvement in a method for the determination of mycophenolic acid in a sample suspected of containing mycophenolic acid. The present invention also provides assay reagents as well as packaged kits useful for performing the methods of the invention.

4 Claims, No Drawings

OTHER PUBLICATIONS

Loralie J. Langman et al., "Blood Distribution of Mycophenolic Acid," *Therapeutic Drug Monitoring: A Journal Devoted to Therapeutic Drug Monitoring and Clinical Drug Toxicology*, vol. 16, No. 6, Dec. 1994, pp. 602–607.

Irena Nowak et al., "Mycophenolic Acid Binding to Human Serum Albumin: Characterization And Relation To Pharmacodynamics," *Clinical Chemistry*, vol. 41, No. 7, 1995, pp. 1011–1017.

Tsina, I., et al., High–performance liquid chromatographic method for the determination of mycophenolate mofetil in human plasma, *Journal of Chromatography B*, 681 (1996) 347–353.

Haley, C.J., et al., Analytical Performance of an Emit Assay for Mycophenolic Acid in Plasma, *Clinical Chemistry*, vol. 43, No. 6, 1997, Abstract No. 474.

Allison A., et al., Mechanisms of Action of Mycophenolic Acid, *Annals of the New York Academy of Sciences*, vol. 696, pp. 63–87, 1993.

Holt, D.W., et al., Monitoring New Immunosuppressive Agents, Are the Methods Adequate?, *Drug Metabolism and Drug Interactions*, vol. 14, No. 1, 1992.

Yatscoff, R.W., et al, Pharmacodynamic Monitoring of Immunosuppressive Drugs, *Transplantation Proceedings*, vol. 28, No. 6 (Dec.) 1996: pp 3013–3015.

* cited by examiner

METHODS FOR RELEASING A LIGAND FROM A COMPLEX

This application claims the benefit of U.S. Provisional Application No. 60/022,133, filed Jul. 18, 1996.

BACKGROUND OF THE INVENTION

1. Field of the Invention

This invention relates to ligand-receptor binding assay techniques. The determination of the presence or concentration of a ligand analyte that is a member of a specific binding pair ("sbp member") consisting of ligand and its complementary receptor, in serum or other body fluids relies increasingly upon specific binding assay techniques. These techniques are based on formation of a complex between sbp members in which one or the other of the complex may be labeled with a moiety that produces a signal either directly or indirectly. In the case of competitive specific binding assay techniques, analyte in a sample of fluid being tested for its presence competes with a known quantity of labeled analyte in binding to a limited amount of a complementary sbp member. Thus, the amount of labeled analyte bound to the sbp member varies inversely with the amount of analyte in the sample. In immunometric assays, the analyte is usually a ligand and the assay employs a complementary sbp member and a second labeled receptor, usually an antibody. In such an assay, the amount of labeled receptor associated with the complex is directly related to the amount of analyte substance in the fluid sample. Numerous variations of the above are also used in the detection of analytes such as the use of a receptor for a receptor for the analyte or other binding pairs such as avidin-biotin and the like.

The presence in the sample of one or more interfering substances such as proteins, e.g., albumin, that bind non-specifically to the analyte in question or to a reagent being employed in an assay for such analyte can be a serious factor in compromising the quantitative character of a ligand-receptor assay. The analyte is usually present in very small amounts. An interfering substance may be present in greater amounts and can bind to a significant number of analyte molecules and, thus, reduce assay sensitivity. In many situations, the amount of interfering substance will vary from sample to sample thereby preventing accurate reference to a standard or calibrator normally employed to provide for translating the observed signal into the concentration of the analyte. In order to enhance the accuracy of an assay, it is desirable to diminish or to completely remove the effect of the interfering substance on the observed signal.

Mycophenolic acid ("MPA") is produced by the fermentation of several penicillium species. It has a broad spectrum of activities, specific mode of action, and is tolerable in large doses with minimal side effects, Epinette, et al., *Journal of the American Academy of Dermatology* 17(6):962–71 (1987). MPA has been shown to have antitumor, antiviral, antipsoriatic, immunosuppressive, anti-inflammatory activities, Lee, et al., *Pharmaceutical Research* 7(2):161–166 (1990), along with antibacterial and antifungal activities, Nelson, et al., *Journal of Medicinal Chemistry* 33(2):833–838 (1990). It inhibits inosine monophosphate dehydrogenase, an enzyme in the de novo synthesis of purine nucleotides (Wu, *Perspectives in Drug Discovery and Design* (1994) 2:185–204). Since T and B lymphocytes depend largely upon this de novo synthesis, MPA is able to inhibit lymphocyte proliferation, which is a major factor of the immune response.

The morpholinoethyl ester of MPA, morpholinoethyl (E)-6-(1,3-dihydro-4-hydroxy-6-methoxy-7-methyl-3-oxo-5-isobenzofuranyl)-4-methyl-4-hexenoate ("MPA-M") is rapidly hydrolyzed in vivo to MPA. Administration of MPA in the form of this ester, greatly improves MPA's bioavailability.

Because MPA is a potent biologically active material, an effective immunoassay could be useful in monitoring its bioavailability. In addition, it may be important to monitor therapeutic drug levels, i.e., optimal drug levels necessary for adequate immunosuppression. Since MPA-M is rapidly hydrolyzed to MPA, an assay for MPA would allow a means of regulating and optimizing MPA-M dosages. It is known that MPA is highly protein-bound in plasma (83>98%) and any factors that alter plasma protein concentrations in patients could affect the accuracy of an MPA assay (Shaw, et al., *Therapeutic Drug Monitoring* (1995) 17:690–699).

Patients under treatment with MPA and cyclosporin or tacrolimus may be co-administered numerous drugs including, but not limited to, azathioprine, prednisonis, methylprednisolone, antivirals, antibiotics, antifungals, cardiovascular agents, diabetic agents and diuretic agents. Many of these drugs have profound effects on metabolism and result in changes in concentrations of various serum/plasma components. There exists, therefore, a potential for interference by these components, either directly or indirectly, in the determination of MPA in the target patient population.

Serum assays in general are limited by the difficulty of variations in plasma protein concentrations in patient populations. Furthermore, variations in sample matrix components that alter free and bound fractions of MPA, such as albumin concentration, can lead to inaccurate immunoassay results without releasing MPA from its bound fraction. In particular, the apparent concentration of MPA would be higher or lower depending on the protein concentration of the sample. For example, in the early post transplant period, albumin concentrations are low relative to a calibrator with normal plasma protein concentrations so that MPA quantitation of these patient samples could be high. A number of factors including time post transplant an metabolic differences due to co-administered drugs or disease states of the patient can result in abnormal protein concentrations. These abnormal protein concentrations may alter the free-to-bound ratio of MPA and, therefore, affect the accuracy of the immunoassay results. Variable recovery as a function of protein concentration of the samples prevents selection of one average protein concentration for calibrators that represents all samples.

Salicylate is known to increase MPA free fraction in normal human plasma when present at concentrations that may be observed in chronic administration of aspirin (Nowak, infra). However, we have found that the use of salicylate as a releasing agent can result in a 25–50% decrease in the total dose-response curve in an MPA enzyme immunoassay. It is also known that 8-anilino-1-naphthalenesulfonic acid (ANS) functions as a releasing agent in immunoassays (Nerli, et al., *Arch Int Physiol Biochim Biophys* (1994) 102(1):5–8 and Seth, et al., *Clin Chem* (1975) 21(10):1406–1413. However, ANS has disadvantages because of its background absorbance at 340 nm and its susceptibility to light degradation. The background absorbance is particularly disadvantageous in enzyme immunoassays. However, ANS has been used in certain enzyme assays under conditions where its disadvantages can be tolerated.

The present invention avoids the deficiencies of the above known compounds used as releasing agents in assays for ligands.

2. Description of the Related Art

Nowak, et al., *Clin. Chem.* (1995) 41(7): 1011–1017 discusses mycophenolic acid binding to human serum albumin: characterization and relation to pharmacodynamics.

Langman, et al., *Therapeutic Drug Monitoring* (1994) 16:602–607 discusses blood distribution of mycophenolic acid.

European Patent 0 218 309 B1 discloses a method for measuring free ligands in biological fluids. Sodium salicylate and 2,4-dinitrophenol were employed to prevent labeled analogs of triiodothyronine and tetraiodothyronine from binding to albumin and thyroid binding pre-albumin.

European Patent Application 0 392 332 A2 discloses a fluorescent polarization immunoassay and reagents therefor. Various compounds were disclosed for converting a marijuana metabolite, which was bound to serum albumin and other proteins in urine, to free form. These compounds included, among others, ANS, salicylic acid and 5-methoxysalicylic acid.

SUMMARY OF THE INVENTION

One aspect of the present invention relates to a method for releasing a ligand from a complex thereof. The method comprises contacting a medium suspected of containing such complex with an effective amount of a compound of the formula:

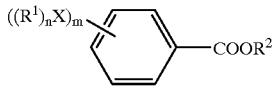

wherein $R^1$ is alkyl; $R^2$ is hydrogen or alkyl; X is O, S or N; n is 1 when X is O or S and n is 2 when X is N; and m is 1 or 2 (Compound I).

Another aspect of the present invention is an improvement in a method for the determination of an analyte that is a member of a specific binding pair in a sample suspected of containing such analyte. The method comprises the steps of (a) providing in an assay medium the sample and a binding partner for the analyte and (b) detecting the binding of the binding partner to the analyte. The improvement comprises including in the assay medium Compound I in an amount sufficient to enhance the accuracy of the determination.

Another embodiment of the present invention relates to a method for releasing mycophenolic acid from a complex thereof. The method comprises contacting a medium suspected of containing the complex with an effective amount of Compound I.

Another embodiment of the present invention is an improvement in a method for the determination of mycophenolic acid in a sample suspected of containing mycophenolic acid. The method comprises (a) providing in an assay medium the sample and a binding partner for mycophenolic acid and (b) detecting the binding of the binding partner to mycophenolic acid. The improvement comprises including in the assay medium Compound I in an amount sufficient to enhance the accuracy of the determination.

A further embodiment of the present invention is an improvement in a method for measuring the amount of mycophenolic acid in a sample suspected of containing mycophenolic acid and endogenous proteins that bind to the mycophenolic acid. The method comprises (a) combining in an aqueous medium the sample, mycophenolic acid conjugated to a detectable label, and an antibody capable of binding to mycophenolic acid, and (b) determining the effect of the sample on the activity of the label. The improvement comprises including in the medium a compound of the formula:

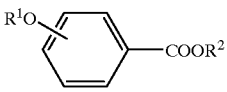

wherein $R^1$ is alkyl and $R^2$ is hydrogen or alkyl (Compound II) in an amount effective in releasing the mycophenolic acid from the endogenous proteins.

The present invention further includes kits for conducting an assay for the determination of an analyte. The kit comprises in packaged combination a binding partner for the analyte and Compound I.

A kit for conducting an assay for the determination of mycophenolic acid comprises in packaged combination an antibody capable of binding to mycophenolic acid, a compound comprising mycophenolic acid bound to a detectable label, and Compound I.

DESCRIPTION OF THE SPECIFIC EMBODIMENTS

Before proceeding with the description of the specific embodiments of the invention, a number of terms will be defined.

Analyte—the compound or composition to be detected. The analyte can be comprised of a member of a specific binding pair (sbp) and may be a ligand, which is usually monovalent (monoepitopic), usually haptenic, and is a single compound or plurality of compounds which share at least one common epitopic or determinant site.

The monoepitopic ligand analytes will generally be from about 100 to 2,000 molecular weight, more usually from 125 to 1,000 molecular weight. The analytes include drugs, metabolites, pesticides, pollutants, and the like. Representative analytes, by way of example and not limitation, include (I) alkaloids such as morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbituates, e.g. phenobarbital and secobarbital, diphenylhydantoin, primidone, ethosuximide, and their metabolites; (iv) aminoalkylbenzenes, with alkyl of from 2 to 3 carbon atoms, which include the amphetamines; catecholamines, which includes ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which includes cannabinol and tetrahydrocannabinol; (viii) hormones such as thyroxine, cortisol, triiodothyronine, testosterone, estradiol, estrone, progestrone, polypeptides such as angiotensin, LHRH, and immunosuppressants such as cyclosporin, tacrolimus, mycophenolic acid (MPA), and so forth; (ix) vitamins such as A, B, e.g. B12, C, D, E and K, folic acid, thiamine; (x) prostaglandins, which differ by the degree and sites of hydroxylation and unsaturation; (xi) tricyclic antidepressants, which include imipramine, dismethylimipramine, amitriptyline, nortriptyline, protriptyline, trimipramine, chlomipramine, doxepine, and desmethyldoxepin; (xii) anti-neoplastics, which include methotrexate; (xiii) antibiotics, which include penicillin, chloromycetin, actinomycetin, tetracycline, terramycin, the metabolites and derivatives; (xiv) nucleosides and nucleotides, which include ATP, NAD, FMN, adenosine, guanosine, thymidine, and cytidine with their appropriate sugar and phosphate substituents; (xv) miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives; (xvi) metabolites related to diseased states include spermine, galactose, phenylpyruvic acid, and porphyrin Type 1; (xvii) aminoglycosides, such as gentamicin, kanamicin, tobramycin, and amikacin; and (xviii) pesticides such as polyhalogenated biphenyls, phosphate esters, thiophosphates, carbamates, polyhalogenated sulfenamides, their metabolites and derivatives.

The present invention may be applied to polyvalent ligand analytes having a site subject to the same non-specific binding as a monovalent analyte. Such polyvalent analytes are normally poly(amino acids) such as polypeptides and proteins, polysaccharides, nucleic acids, and combinations thereof. Such combinations include components of bacteria, viruses, chromosomes, genes, mitochondria, nuclei, cell membranes and the like.

The term analyte can further include oligonucleotide and polynucleotide analytes such as m-RNA, r-RNA, t-RNA, DNA, DNA-RNA duplexes, etc.

The analyte may be a molecule found directly in a sample such as biological tissue, including body fluids, from a host. The sample can be examined directly or may be pretreated to render the analyte more readily detectable by removing unwanted materials. The sample may be pretreated to separate or lyse cells; precipitate, hydrolyze or denature proteins; hydrolyze lipids; solubilize the analyte; or the like. Such pretreatment may include, without limitation: centrifugation; treatment of the sample with an organic solvent, for example, an alcohol, such as methanol; and treatment with detergents. The sample can be prepared in any convenient medium which does not interfere with the assay. An aqueous medium is preferred.

Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay.

The biological tissue includes excised tissue from an organ or other body part of a host and body fluids, for example, urine, whole blood, plasma, serum, saliva, semen, stool, sputum, cerebral spinal fluid, tears, mucus, and the like. Preferably, the sample is plasma or serum.

Mycophenolate ester—includes, but is not limited to, esters of MPA at the carboxylic acid group of the side chain attached at the 1'-position of the MPA isobenzofuranyl ring system such as MPA-M.

MPA metabolite—a product of the metabolism of MPA, preferably a product containing the isobenzofuranyl ring system, more preferably products also containing a portion of the side chain such as the acyl or phenolic glucuronide of MPA.

Measuring the amount of an analyte—quantitative, semiquantitative, and qualitative methods as well as all other methods for determining an analyte are considered to be methods of measuring the amount of an analyte. For example, a method which merely detects the presence or absence of an analyte in a sample suspected of containing the analyte is considered to be included within the scope of the present invention. The terms "detecting" and determining as well as other common synonyms for measuring, are contemplated within the scope of the present invention.

Capable of distinguishing between—the ability of a receptor or antibody to bind preferentially to a first ligand relative to a second ligand. Usually at least 5-fold more of the first ligand than the second ligand will be bound when the antibody is combined with a sample containing the ligands. Preferably, at least 10-fold more and, more preferably, at least 20-fold more of the first ligand will be bound. Although the relative binding of each ligand will depend on the relative concentrations in the sample, usually these conditions are met when the binding constant of the antibody to the first ligand is at least equal to the binding constant to the second ligand, and preferably, is at least 10-fold, more preferably, at least 50-fold the binding constant to the second ligand.

Conjugate—a molecule comprised of two or more molecules bound together, optionally through a linking group, to form a single structure. The binding can be made either by a direct connection (e.g. a chemical bond) between the molecules or by use of a linking group. For example, an analyte analog conjugated to an enzyme is an analyte analog-enzyme conjugate.

Member of a specific binding pair ("sbp" member)—one of two different molecules having an area on the surface or in a cavity that specifically binds to and is therefore defined as complementary with a particular spatial and polar organization of the other molecule. The members of the sbp can be referred to as ligand and receptor such as members of an immunological pair, e.g., antigen-antibody. Complementary sbp members bind to one another, as for example, a ligand and its complementary receptor. With respect to two complementary sbp members, one may be referred to as the "binding partner" for the other. Sbp members can be immunological pairs such as antigen and antibody, or non-immunological pairs such as avidin and biotin. Sbp members can also be small molecules or residues of small molecules and their receptors. Small molecules have a molecular weight of from 100–2000, preferably 150–1000, and a receptor for the small molecule either exists or can be prepared. Examples of small molecules include derivatives of biotin, lysergic acid, fluorescein or a fluorescein derivative, and vitamin $B_{12}$, with the corresponding receptors being avidin or streptavidin, anti-lysergic acid, anti-fluorescein and intrinsic factor, respectively. Small molecules are often covalently bound to other sbp members to form a conjugate having at least one, and frequently 2–20, small molecules. Bonding of the small molecule to the sbp member may be accomplished by chemical reactions which result in replacing a hydrogen atom of the small molecule with a bond to the sbp member or by a linking group between the small molecule and the sbp member of any size but preferably no larger than necessary to permit binding to the conjugate of both a receptor for the small molecule and the sbp member.

Ligand—any organic compound for which a receptor naturally exists or can be prepared.

Ligand analog (or analyte analog)—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Specific binding—the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

Non-specific binding—non-covalent binding between molecules that is relatively independent of specific surface structures. Non-specific binding may result from several factors including hydrophobic interactions between molecules.

Non-specific complex of a ligand—a ligand bound non-specifically to another substance, usually, endogenous substances present in a sample to be analyzed. The endogenous substances generally are endogenous proteins such as plasma proteins, e.g., albumin, globulins, glycoproteins, lipoproteins, and the like.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7:1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Kohler and Milstein, Nature 256:495–497,1975. Reviews of monoclonal antibody techniques are found in Lymphocyte Hybridomas, ed. Melchers, et al. Springer-Verlag (New York 1978), Nature 266: 495 (1977), Science 208: 693 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Kohler and Milstein, supra).

In another approach for the preparation of antibodies the sequence coding for antibody binding sites can be excised from the chromosome DNA and inserted into a cloning vector which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

Hapten—a compound capable of binding specifically to corresponding antibodies, but do not themselves act as immunogens (or antigens) for preparation of the antibodies. Antibodies which recognize a hapten can be prepared against compounds comprised of the hapten linked to an immunogenic (or antigenic) carrier. Haptens are a subset of ligands.

MPA analog—modified MPA. The modification provides means to join this analog to another molecule. The analog will usually differ from MPA by more than replacement of a hydrogen with a bond which links the analog to a hub or label.

Immunogenic carrier—a group which, when conjugated to a hapten and injected into a mammal, will induce an immune response and elicit the production of antibodies that bind to the hapten, in this case MPA. Immunogenic carriers are also referred to as antigenic carriers. Typical immunogenic carriers include, without limitation, poly(amino acids), polysaccharides, nucleic acids and particles (biologic and synthetic materials). A wide variety of such carriers are disclosed in Davalian, et al., U.S. Pat. No. 5,089,390, column 4, line 57 to column 5, line 5, incorporated herein by reference. Other suitable immunogenic carriers include albumins, serum proteins, e.g., globulins, ocular lens proteins and lipoproteins. Illustrative proteins include bovine serum albumin, keyhole limpet hemocyanin ("KLH"), ovalbumin and bovine gamma-globulin.

Support or surface—a solid phase, typically a support or surface, which is a porous or non-porous water insoluble material that can have any one of a number of shapes, such as strip, rod, plate, well, particle and bead. A wide variety of suitable supports are disclosed in Ullman, et al. U.S. Pat. No. 5,185,243, columns 10–11, Kum, et al., U.S. Pat. No. 4,868,104, column 6, lines 21–42 and Milbum, et al., U.S. Pat. No. 4,959,303, column 6, lines 14–31, which are incorporated herein by reference. Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). As used herein, the term "capable of being bound to a support" means, for example, that a reagent, such as the anti-analyte antibody, is bound to a first sbp member or a small molecule and a complementary second sbp member or receptor for the small molecule, is in turn bound a support. Alternately, a receptor for the anti-analyte antibody, such as an anti-mouse antibody, is bound to a support and used to capture the anti-analyte antibody. Therefore, the anti-analyte antibody is not actually bound to a support, but will become bound, when a complementary sbp member or receptor is added.

Signal producing system ("sps")—one or more components, at least one component being a detectable label, which generate a detectable signal that relates to the amount of bound and/or unbound label, i.e. the amount of label bound or not bound to the compound being detected. The label is any molecule that produces or can be induced to produce a signal, and preferably is a fluorescer, radiolabel, enzyme, chemiluminescer or photosensitizer. Thus, the signal is detected and/or measured by detecting fluorescence or luminescence, radioactivity, enzyme activity or light absorbance.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, rhodamine compounds, phycoerythrin, phycocyanin, allophycocyanin, o-phthaldehyde, and fluorescamine; chemiluminescers such as isoluminol; sensitizers; coenzymes; enzyme substrates; radiolabels such as $^{125}I$, $^{131}I$, $^{14}C$, $^{3}H$, $^{57}Co$ and $^{75}Se$; particles such as latex or carbon particles; metal sol; crystallite; liposomes; cells, etc., which may be further labeled with a dye, catalyst or other detectable group. Suitable enzymes and coenzymes are disclosed in Litman, etal., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

There are numerous methods by which the label can produce a signal detectable by external means, for example, by visual examination, electromagnetic radiation, heat, and chemical reagents. The label or other sps members can also be bound to an sbp member, another molecule or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes. Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, columns 11–13, incorporated herein by reference.

The label can be bound covalently to numerous sbp members: an antibody; a receptor for an antibody; a receptor that is capable of binding to a small molecule conjugated to an antibody; or a ligand analog. Bonding of the label to the sbp member may be accomplished by chemical reactions which result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See for example, Rubenstein, et al., U.S. Pat. No. 3,817,837, incorporated herein by reference. This invention also contemplates having an antibody bound to a first sps member and a detectable label as the second sps member. For example, when the detectable label is bound to a ligand analog, the extent of binding of the antibody to the analog can be measured by detecting the signal produced by the interaction of the sps members.

Ancillary Materials—Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly nonionic surfactants, binding enhancers, e.g., polyalkylene glycols, preservatives, antimicrobials, or the like.

Linking Group—a portion of a structure which connects 2 or more substructures. The linking group can be a bond or it can have at least 1 uninterrupted chain of atoms other than hydrogen (or other monovalent atoms) extending between the substructures. The number of atoms in the chain will be at least one and is determined by counting the number of atoms other than hydrogen along the shortest route between the substructures being connected, and is typically 1–30, usually 2–10, preferably 3–8, atoms each independently selected from the group consisting of carbon, oxygen, nitrogen, sulfur and phosphorous. The number of total atoms in the linking group is determined by counting the total carbon, oxygen, nitrogen, sulfur and phosphorous atoms, i.e. the atoms other than hydrogen. Typically, the linking group has a total of less than 30 atoms, preferably less than 20 atoms, more preferably less than 10 atoms. As a general rule, the length of a particular linking group can be selected arbitrarily to provide for convenience of synthesis and the incorporation of any desired group. The linking groups may be aliphatic or aromatic, although with diazo groups, aromatic groups will usually be involved. Oxygen will normally be present as oxo or oxy, bonded to carbon, sulfur, nitrogen or phosphorous; nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, dithiol, ether, urea, thiourea, guanidine, azo, thioether and carboxylate, sulfonate, and phosphate esters, amides and thioesters.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

One aspect of the present invention relates to a method for releasing a ligand from a non-specific complex thereof such as a complex wherein the ligand is bound non-specifically to another substance such as endogenous sample proteins and their non-specific substances. The method comprises contacting a medium suspected of containing such complex with an effective amount of Compound I.

Representative examples of compounds having the above formula are found in Table 1, by way of illustration and not limitation.

TABLE 1

| Compound | X | $R^1$ | $R^2$ | n | m | Ring position* |
|---|---|---|---|---|---|---|
| I-A | O | alkyl | H | 1 | 2 | ortho |
| I-B | O | alkyl | H | 1 | 2 | meta |
| I-C | O | alkyl | alkyl | 1 | 2 | ortho |
| I-D | O | alkyl | alkyl | 1 | 2 | meta |
| I-E | S | alkyl | H | 1 | 2 | ortho |
| I-F | S | alkyl | H | 1 | 2 | meta |
| I-G | S | alkyl | alkyl | 1 | 2 | ortho |
| I-H | S | alkyl | alkyl | 1 | 2 | meta |
| I-I | N | alkyl | H | 2 | 2 | ortho |
| I-J | N | alkyl | H | 2 | 2 | meta |
| I-K | N | alkyl | alkyl | 2 | 2 | ortho |
| I-L | N | alkyl | alkyl | 2 | 2 | meta |
| I-M | O | alkyl | H | 1 | 1 | ortho |
| I-N | O | alkyl | H | 1 | 1 | meta |
| I-O | O | alkyl | H | 1 | 1 | para |
| I-P | O | alkyl | alkyl | 1 | 1 | ortho |
| I-Q | O | alkyl | alkyl | 1 | 1 | meta |
| I-R | O | alkyl | alkyl | 1 | 1 | para |
| I-S | S | alkyl | H | 1 | 1 | ortho |
| I-T | S | alkyl | H | 1 | 1 | meta |
| I-U | S | alkyl | H | 1 | 1 | para |

TABLE 1-continued

| Compound | X | $R^1$ | $R^2$ | n | m | Ring position* |
|---|---|---|---|---|---|---|
| I-V | S | alkyl | alkyl | 1 | 1 | ortho |
| I-W | S | alkyl | alkyl | 1 | 1 | meta |
| I-X | S | alkyl | alkyl | 1 | 1 | para |
| I-Y | N | alkyl | H | 2 | 1 | ortho |
| I-Z | N | alkyl | H | 2 | 1 | meta |
| I-AA | N | alkyl | H | 2 | 1 | para |
| I-BB | N | alkyl | alkyl | 2 | 1 | ortho |
| I-CC | N | alkyl | alkyl | 2 | 1 | meta |
| I-DD | N | alkyl | alkyl | 2 | 1 | para |

*Ring position refers to the position on the benzene ring of the --$XR^1$ group in relation to the carboxy group.

Preferably, compounds for use in the methods of the present invention have an ortho relationship between the carboxy group and the substituent —$XR^1$ and have the formula (designated Compounds I'):

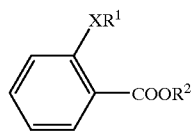

wherein $R^1$ is alkyl; $R^2$ is hydrogen or alkyl; X is O, S or N. Representative compounds in this category, by way of example and not limitation, are Compounds I-M, I-P, I-S, I-V, I-Y and I-BB above.

Preferred compounds of formula I above are those of the formula of Compound II. Representative compounds in this group, by way of illustration and not limitation, are Compounds I-M, I-N, I-O, I-P, I-Q and I-R above.

More preferably, compounds useful in the present invention are those of the following formula (Compound III):

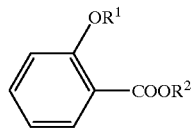

wherein $R^1$ is alkyl and $R^2$ is hydrogen or alkyl. Representative compounds in this group, by way of illustration and not limitation, are Compounds I-M and I-P above. Particularly preferred compounds with this category are those wherein $R^1$ is lower alkyl, more preferably, methyl.

More preferred are compounds of the following formula (Compounds IV):

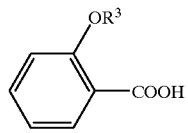

wherein $R^3$ is lower alkyl. Particularly preferred is o-methoxybenzoic acid also known as o-anisic acid.

It is important in the present invention that the particular Compound I employed not bind to any significant degree to an sbp member or binding partner for an analyte used in an assay for the analyte. What constitutes a significant degree is dependent on the sensitivity necessary for the assay; the higher the sensitivity required for the assay, the less tolerable is the amount of binding between an sbp member or binding partner for the analyte. By the term "significant degree" is meant that the particular Compound I not bind to an sbp member or binding partner to an extent that would affect the accuracy or the quantitative or qualitative nature of the assay result. Accordingly, any binding between a particular Compound I and an sbp member or a binding partner should be, preferably, less than 1%, more preferably, less than 0.01%, most preferably 0%. Such percentage is determined by measuring the apparent analyte quantitation of the given amount of releasing agent and expressing the result as a fraction of the actual concentration. Furthermore, the particular Compound I selected must have minimal, if any, interference with the binding of sbp members to one another or with the ability of the signal producing system to produce a signal in relation to the presence or amount of analyte in a sample.

By the term "effective amount" is meant an amount sufficient to bring about the release of the ligand from such complex so that preferably at least about 90%, more preferably, at least 99% and most preferably 100% of the ligand is in a form free of such complex. The effective amount of Compound I to be used in a particular assay will depend on the nature of the ligand and of the assay and reagents employed therein. Preferably, the effective amount is determined empirically based on the suspected concentration range of analyte in the sample. In general, an effective amount of Compound I is an excess amount over the suspected amount of the analyte. Considering an assay for MPA, by way of illustration and not limitation, where the expected level of drug in a sample is about 1.5 to 45 $\mu$M, the effective amount of Compound I in the assay medium is about 0.1 to about 100 mM, preferably, about 1 to about 25 mM, more preferably, about 2 to 12 mM.

Many of the compounds useful in the present invention are commercially available and/or their synthesis is known in the literature. The compounds useful in the methods of the present invention may be prepared by known procedures from starting materials that are readily available such as benzoic acid or hydroxybenzoic acid. Such procedures involve formation of one or more alkoxy groups on the benzene ring and esterification of the resulting compound where an ester is desired. Both of the above may be accomplished by well-known procedures that will not be repeated here. See, for example, Heathcock, et al., "Introduction to Organic Chemistry," MacMillan Publishing Company, New York, N.Y., Third edition, 1985, pages 814 and 493; Carey, "Organic Chemistry," McGraw Hill Inc., New York, N.Y., First edition, 1987, pages 994–995 and 609.

The method of the present invention may be applied to most assays for the determination of an analyte that is an sbp member, particularly those for the determination of free analyte, e.g., free hapten. In general, a sample suspected of containing an analyte is combined in an assay medium with a binding partner for the analyte and other reagents depending on the particular assay performed. The binding of the binding partner to the analyte, if present, is detected. An effective amount of Compound I is included in the assay medium. The assay can be performed either without separation (homogeneous) or with separation (heterogeneous) of any of the assay components or products. Homogeneous immunoassays are exemplified by the EMIT® assay products (Behring Diagnostics Inc., formerly Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59 to column 23, line 25; enzyme channeling techniques such as those disclosed in Maggio, et al., U.S. Pat. No. 4,233,402, column 6, line 25 to column 9, line 63; and other enzyme immunoassays such as the enzyme linked immunosorbant assay ("ELISA") are discussed in Maggio, E. T. supra. Exemplary of heterogeneous assays are the radioimmunoassay, disclosed in Yalow, et al., *J. Clin. Invest.* 39:1157 (1960). The above disclosures are all incorporated herein by reference.

A typical non-competitive sandwich assay is an assay disclosed in David, et al., U.S. Pat. No. 4,486,530, column 8, line 6 to column 15, line 63, incorporated herein by reference. In this method, an immune sandwich complex is formed in an assay medium containing an effective amount of Compound I. The complex comprises the analyte, a first antibody (monoclonal or polyclonal) that binds to the analyte and a second antibody that binds to the analyte or a complex of the analyte and the first antibody. Subsequently, the immune sandwich complex is detected and is related to the amount of analyte in the sample. The immune sandwich complex is detected by virtue of the presence in the complex of a label wherein either or both the first antibody and the second antibody contain labels or substituents capable of combining with labels, such as, for example, providing the antibody linked to biotin and providing avidin bound to a label.

Another method that is useful in carrying out the assay of this invention is disclosed in Ullman, et al., U.S. Pat. No. 4,857,453, column 11, line 21 to column 14, line 42, and column 18, line 21 to column 21, line 55, incorporated herein by reference.

The assay is normally carried out in an aqueous buffered medium at a moderate pH, generally that which provides optimum assay sensitivity. The aqueous medium may be solely water or may include some percentage of a cosolvent, for example, from 0–40 volume percent of a cosolvent. The pH for the medium will usually be in the range of 4–11, more usually in the range of 5–10, and preferably in the range of 6.5–9.5.

The pH will usually be a compromise between optimum binding of the binding members of any specific binding pairs, optimum release of the analyte from a non-specific complex thereof in accordance with the present invention, and the pH optimum for other reagents of the assay such as members of the signal producing system.

Various buffers may be used to achieve the desired pH and maintain the pH during the determination. Illustrative buffers include borate, phosphate, carbonate, tris and barbital. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from 5–45° C., more usually from 15–40° C. Temperatures during measurements will generally range from 10–50° C., more usually from 15–40° C.

The concentration of analyte that may be assayed will generally vary from $10^{-4}$ to $10^{-13}$ M, more usually from $10^{-5}$ to $10^{-7}$ M. Considerations, such as whether the assay is qualitative, semiquantitative or quantitative (relative to the amount of analyte present in the sample), the particular detection technique and the concentration of the analyte will normally determine the concentrations of the various reagents.

The concentrations of the various reagents in the assay medium will generally be determined by the concentration range of interest of the analyte. However, the final concentration of each of the reagents will normally be determined empirically to optimize the sensitivity of the assay over the range. That is, a variation in concentration of analyte which is of significance should provide an accurately measurable signal difference.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition, generally ranging from 30 seconds to 6 hours, more usually from 1 minute to 1 hour.

The following examples further describe the specific embodiments of the invention, and are intended to describe and not to limit the scope of the invention. MPA assays are referred to by way of example and not limitation.

In a homogeneous assay after all of the reagents have been combined, the signal is determined and related to the amount of MPA in the sample. For example, in an EMIT assay for MPA, a sample suspected of containing MPA is combined in an aqueous medium either simultaneously or sequentially with an MPA-enzyme conjugate and antibody capable of recognizing MPA and the conjugate. The medium also contains an effective amount of Compound I. Generally, a substrate for the enzyme is added which results in the formation of a chromogenic or fluorogenic product upon enzyme catalyzed reaction. Preferred enzymes are glucose-6-phosphate dehydrogenase and alkaline phosphatase. Compound I acts to release MPA from any non-specific complex thereof that may be present in the sample. The MPA and the MPA-enzyme conjugate compete for binding sites on the antibody. The enzyme activity in the medium is then determined, usually by spectrophotometric means, and is compared to the enzyme activity determined when calibrators or reference samples are tested in which a known amount of MPA is present. Typically, the calibrators are tested in a manner similar to the testing of the sample suspected of containing MPA. The calibrators will typically contain differing, but known, concentrations of the MPA analyte to be determined. Preferably, the concentration ranges present in the calibrators will span the range of suspected MPA concentrations in the unknown samples.

Heterogeneous assays usually involve one or more separation steps and can big competitive or non-competitive. A variety of competitive and non-competitive assay formats are disclosed in Davalian, et al., U.S. Pat. No. 5,089,390, column 14, line 25, to column 15, line 9, incorporated herein by reference. In a typical competitive assay a support having an antibody for MPA bound thereto is contacted with a medium containing the sample and MPA conjugated to a detectable label such as an enzyme. The medium also contains an effective amount of Compound I. MPA in the sample competes with the conjugate for binding to the antibody. After separating the support and the medium, the label activity of the support or the medium is determined by conventional techniques and related to the amount of MPA in the sample.

As mentioned above, the present invention provides advantages over known compounds for releasing analytes from non-specific binding substances present in samples for analysis. With the present invention up to 100% of the analyte can be released from endogenous non-specific binding substances such as plasma proteins. Thus, variable recovery of the analyte as a function of protein concentration relative to a calibrator matrix is substantially reduced or eliminated. Furthermore, variable recovery of analyte as a function of the presence of co-administered drugs is substantially reduced or eliminated because competition for binding sites on endogenous non-specific binding substances between an analyte and other drugs that bind to such substances is reduced or eliminated. High background absorbance associated with some of the known agents is avoided in the present invention. Accordingly, the present methods provide particular advantages for assays wherein a signal producing system is used that produces signal in the range of about 300 to about 700 nm. This is an important advantage particularly for spectrophotometric based immunoassays. Yet another advantage of the use of compounds of the present invention is the avoidance of deleterious effects on the total dose response curves otherwise obtained in assays not utilizing the present compounds. Still another advantage of the present invention is that the present releasing agent does not exhibit light sensitive degradation.

In one MPA assay in accordance with the present invention, antibodies are employed that are capable of binding to MPA and to its esters and metabolites. In another MPA assay in accordance with the present invention, antibodies are used that are capable of distinguishing between MPA and mycophenolate esters, such as MPA-M. In another embodiment of an MPA assay in accordance with the invention, the antibodies employed are able to distinguish between MPA and MPA metabolites, such as MPA-G.

The binding of the antibody to MPA can be detected in numerous ways that are well known in the art. Binding of the antibody and MPA forms an immune complex that can be detected directly or indirectly. The immune complexes are detected directly, for example, when the antibodies employed are conjugated to a label. The immune complex is detected indirectly by examining for the effect of immune complex formation in an assay medium on a signal producing system or by employing a labeled receptor that specifically binds to an antibody of the invention.

Another aspect of the present invention relates to kits useful for conveniently performing an assay for the determination of an analyte. A kit in accordance with the present invention comprises in packaged combination a binding partner for the analyte and Compound I. The kit may further comprise a conjugate of the analyte bound to a detectable label. A kit for the determination of a MPA comprises in packaged combination an antibody capable of binding to MPA, a conjugate of MPA and a label, and Compound I.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents. For example, an aqueous solution of a Compound I can be provided in a separate container. Alternatively, a Compound I can be included in one of the reagents for conducting an assay. For example, Compound I can be included in an aqueous medium containing an antibody reagent; such aqueous medium can be packaged in a separate container.

The kit can further include other separately packaged reagents for conducting an assay such as additional sbp members, ancillary reagents such as an ancillary enzyme substrate, and so forth. The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

EXAMPLES

The invention is demonstrated further by the following illustrative examples. Parts and percentages herein are by weight unless otherwise indicated. Temperatures are in degrees Centigrade (° C.).

Example 1

Ortho-anisic Acid as a Releasing Agent in an Assay for MPA

The following reagents were prepared:

| # | COMPONENT | % Comp. (by weight) | Comp. by wt./vol. (g/L) (at 20 C°) | COMPONENT SOURCE |
|---|---|---|---|---|
| | | REAGENT A | | |
| 1 | NAD | 2.346 | 23.88 | Boehringer Mannheim |
| 2 | G6P | 0.615 | 6.26 | Calzyme |
| 3 | sodium chloride | 0.491 | 5.00 | Mallinckrodt |
| 4 | MIT | 0.098 | 1.00 | Boehringer Mannheim |
| 5 | Na2 EDTA | 0.036 | 0.37 | Sigma |
| 6 | PLURONIC ® 25R2 | 0.010 | 0.1028 | BASF Chemicals |
| 7 | o-anisic acid | 0.149 | 1.52 | Sigma |
| 8 | BSA | 0.098 | 1.00 | Miles Diagnostics |
| 9 | sodium azide | 0.092 | 0.94 | Amersham USB |
| 10 | Antibody to MPA | 0.001 | 0.0075 | (1) |
| 11 | water | 96.062 | 977.82 | Millipore deionized |
| | | 100.00 | 1017.9 | |
| | pH | 5.6 ± 0.1 | | |
| | | REAGENT B | | |
| 12 | Tris Base | 2.120 | 21.54 | Sigma |
| 13 | Tris HCl | 3.447 | 35.02 | Sigma |
| 14 | BLG | 0.098 | 1.00 | International Enzymes |
| 15 | Na2 EDTA | 0.036 | 0.37 | Sigma |
| 16 | MIT | 0.098 | 1.00 | Boehringer Mannheim |
| 17 | sodium azide | 0.093 | 0.94 | Amersham USB |
| 18 | PLURONIC ® 25R2 | 0.030 | 0.3084 | BASF Chemicals |
| 19 | MPA-G6PDH | 0.00005 | 0.0005 | (2) |
| 20 | Stabilizing antibody | 0.00007 | 0.00075 | (1) |
| 21 | water | 94.077 | 955.92 | Millipore deionized |
| | | 100.000 | 1016.1 | |
| | pH | 8.15 ± 0.15 | | |

(1) Prepared in a manner similar to that described by Galfre, et al., (1981) Preparation of monoclonal antibodies: strategies and procedures, Methods Enzymol. 73: 3–46
(2) Prepared in a manner similar to that described by Grabarek, et al. (1990) Zero-length crosslinking procedure with the use of active esters. Anal. Biochem. 185: 131–135.
PLURONIC ® is a registered trademark of BASF Corporation for block copolymer surfactants.
Abbreviations -continued

| # | COMPONENT | % Comp. (by weight) | Comp. by wt./vol. (g/L) (at 20 C°) | COMPONENT SOURCE |
|---|---|---|---|---|

NAD: nicotinamide adenine dinucleotide
G6P: D-glucose-6-phosphate, monosodium salt
o-anisic acid: o-methoxybenzoic acid
BSA: bovine serum albumin
Na2 EDTA: ethylenediaminetetraacetic acid, disodium salt, dihydrate
MIT: N-methylisothiazolone, hydrochloride
MPA: mycophenolic acid
Tris Base: tris(hydroxymethyl)aminomethane
Tris HCl: Tris hydrochloride
BLG: β-lactoglobulin
MPA-G6PDH: mycophenolic acid conjugated to glucose-6-phosphate dehydrogenase Reagents A and B were prepared as follows.

A 1.028% weight per weight solution of PLURONIC® 25R2 was prepared at 2 to 25° C. for use in both reagents.

Reagent A was prepared by first making an anisic acid solution. Anisic acid was dissolved in 1N NaOH in an amount equal to 25 mL per 1.52 grams of anisic acid. In a separate container was weighed 70% of the final weight of deionized water, to which was added components 1 through 5 inclusive and also component 6 using the prepared solution of PLURONIC® 25R2 at 10 mL thereof per 1017.9 g (or 1.0 liter) of final solution. This solution was stirred and the anisic acid solution was added. If necessary, the pH of the preparation was adjusted within the range of 5.50 to 5.70 with 6 N NaOH. Next, components 8 and 9 were added and the solution was stirred. If necessary, the pH was adjusted to the above range. The solution was then brought to the final weight with deionized water and was filtered through a 0.2 micron filter. Final pH was 5.50 to 5.70. The resulting solution was designated the A diluent. Reagent A was completed by adding antibody, i.e., component 10, to the A diluent to a final antibody concentration of 7.5 mg/L (or 7.5 µg/mL).

It is noted that Reagent A contained BSA, which like human serum albumin binds MPA. However, the BSA was found to be a preferred stabilizer of Reagent A over certain other proteins that were evaluated, and thus was included in Reagent A for this reason. Any releasing agent for MPA, therefore, would be formulated to overcome this effect of BSA as well as any binding from the sample being analyzed. The above formulation had greater than a 500-molar excess of o-anisic acid to BSA in Reagent A. This concentration of o-anisic acid was found to be more than sufficient to release all MPA in the system and keep it displaced.

For Reagent B deionized water was weighed in an amount equal to 80% of the final weight. To this water was added with stirring components 12 through 17 inclusive as well as component 18, using 30 mL of Pluronic 25R2 solution per 1016.1 g (or 1.0 liter) of final solution. The solution was brought to the final weight with deionized water, pH in the range of 8.0 to 8.3, and was filtered through 0.2 micron filter. The solution at this point was designated the B diluent, which was used to make Reagent B by addition of relatively negligible volumes or weights of components 19 and 20. For example 0.37 mL of stabilizing antibody at 20.6 mg/mL and 6.1 mL of conjugate at 0.8 mg/mL were added to 10 L (or 10.18 kg) of Reagent B. The stabilizing antibody, component 20, was added to a final concentration of 0.75 mg/L (or 0.75 µg/mL). The conjugate, component 19, was added to achieve a rate of 300±10 mA/min; rate is defined as the change in absorbance at 340 nm per minute of reaction time and is usually expressed as mA/min.

Rates were determined on a Cobas Mira Plus® instrument (Roche Diagnostics Systems, Inc., Branchburg, N.J.). The temperature was kept at 37° C. for the entire assay. Timings were carried out in cycles with each cycle being 25 seconds. In cycle 1, the first cycle, 75 μL of water and 3 μL of a sample were mixed with 155 μL of A diluent in a 0.6 cm path length cuvette. This mixture was incubated until the addition of Reagent B in cycle 7. To establish the conjugate rate, the sample used did not contain any MPA. In cycle 7, seventy-five μL of Reagent B followed by 20 μL of water was then added to the cuvette, mixed, and incubated until the end of cycle 25 at which time the assay was finished. During the assay, absorbance readings at 340 nm were made at the end of every cycle. A best linear fit was then made using only the 12 consecutive absorbance readings of cycles 14 through 25 versus time in minutes. The slope of this line was the rate.

Reagent A preparations were then made by adding antibody at different levels to the A diluent. These titration levels were then run with Reagent B and calibrators with different levels of MPA (e.g., 0, 0.5, 2.0, 5.0, 10.0, and 15.0 μg/mL). The level of antibody giving the maximum rate separations between the two low end calibrators and between the two high end calibrators was then used to formulate the final Reagent A.

Once Reagent A and B were prepared they were used along with calibrators to determine unknown concentrations of MPA.

To determine an unknown MPA concentration, calibrators were run with Reagents A and B, and rates were determined for each as previously described, except that Reagent A containing antibody was substituted for the A diluent. Duplicate rates were typically determined for each calibrator and averaged. The calibration curve parameters were calculated using the MPA concentrations, average calibrator rates and an appropriate mathematical model such as a logit/log 4 model fit. The fit can be made on line by the analyzer or by appropriate computer programs which optimize the parameters Ro, Kc, a and b in the following equation:

$$R = Ro + \frac{Kc}{1 + \exp[-(a + b \cdot LnC)]}$$

where $Ro, Kc, a, b$ are curve parameters
$C$ is the MPA concentration
$R$ is the rate observed with the MPA concentration Solving this equation for C allowed the unknown MPA concentration to be determined from its rate, R, and the curve parameters as:

$$C = \exp[[a + ln[Kc/(R-Ro) - 1.0]]/-b]$$

The results are summarized as follows:

The effectiveness of the formulation with o-anisic acid was evaluated by measuring the agreement between the quantitation of a 10 μg/mL MPA spike in a normal human plasma pool (NHP) and the quantitation of a similar spike into Dulbecco's phosphate buffered saline (PBS), purchased from BioWhittaker, Walkersville, Md. For both NHP and PBS, two separate spikes were made. PBS contained 0.2 g/L KCl, 0.2 g/L $KH_2PO_4$, 2.16 g/L $Na_2HPO_4 \cdot 7H_2O$, and 8.0 g/L NaCl at a final pH 6.4 to 7.6. The PBS had no protein and thus no protein binding of MPA can occur. Calibrators were NHP with 7 levels of MPA at 0, 0.3, 0.5, 2.5, 5, 10, and 20 μg/mL. The NHP and PBS spikes quantitated nearly the same, giving respective averages of 10.2 and 10.4 μg/mL MPA (pooled standard deviation (sd)=0.4 μg/mL). These results indicate that the method was measuring total MPA and was not affected by normal serum albumin binding of MPA.

Example 2

Comparison of Anisic Acid Isomers and ANS as Releasing Agents in an MPA Assay

In this example four agents, o-anisic acid (o-M), its meta (m-AA) and para (p-M) isomers, and the known releasing agent 8-anilino-1-naphthalene sulfonic acid (ANS) were compared. All the anisic acids were purchased from Sigma Chemical Company, St. Louis, Mo.; the ANS was obtained from Calbiochem, La Jolla, Calif.

In these experiments, the diluent for Reagent A (Rgt A) was made somewhat differently than that in Example 1. However, the composition was the same, except for component 7 (releasing agent, o-anisic acid) and component 10 (concentration of MPA antibody). Five diluents were prepared, four with one of each of the above agents and one control with no agent. First, a 2× solution was made in the manner described in Example 1 but which had only components 1 through 5 and 9 at twice the amounts listed. Next, for three of the diluents, each of the three anisic acid isomers was weighed to achieve a final molarity of 12.5 mM and predissolved in one quarter the final volume of water and a minimum amount of 6 N NaOH (approximately 6 drops per 0.2 grams anisic acid). For the fourth diluent, the agent, ANS, was weighed to give a 0.25 mM final concentration and added to one quarter the final volume of water. The fifth diluent, the control, had no releasing agent. To make each of these five diluents, the appropriate amounts of the 2× solution, the 1× amount of BSA, component 8, and the 1× amount of the Pluronic 25R solution, component 6, were combined. Four of these then received the appropriate agent. All were mixed well. Where necessary, pH adjustments were made as described previously and each preparation was brought to the final volume with deionized water to achieve 1× concentrations of components. Each of these A diluents was then filtered through a 0.2 micron filter. Final pH measurements on each were all between 5.5 to 5.7. For each of these five A diluents, a corresponding Reagent A was made by adding antibody to MPA for a final concentration of 6.5 μg/mL. Reagent B (Rgt B) was prepared as described in Example 1 except that component 20 was omitted and 0.1% BSA (Miles Diagnostics, Kankakee, Ill.) was substituted for BLG.

It should be noted that the concentration of ANS in Reagent A was limited due to its contribution to background absorbance. Higher concentrations of ANS created an offscale absorbance reading, preventing the collection of rate data. It should be further noted that all of the Reagent A preparations were visually colorless except for the Reagent A with ANS which had a tannish yellow color.

In a total of two runs the effects of each of the four agents relative to a control of no agent was examined with respect to (1) background absorbance at 340 nm, (2) the rate of a negative MPA sample, (3) the rate span between 0 and 10 μg/mL MPA, and (4) the closeness of rate matching of a 10 μg/mL MPA spike in NHP and in buffer. Both runs included the control Reagent A. The first run evaluated Reagent A with ANS while the second run evaluated Reagent A preparations containing the structural isomers of anisic acid.

MPA was spiked into NHP and buffer (Buff) to achieve a final concentration of 10 μg/mL MPA. Buffer in this example was 50 mM MES (2-[N-morpholino]-ethanesulfonic acid, obtained from Sigma Chemical Company) with 0.1% (weight/volume) sodium azide, pH 7.1. As with PBS, this buffer has no protein and thus no protein binding of MPA can occur.

In both runs, the background absorbance at 340 nm for each Reagent A was measured in duplicate on a 230-μL combination of 3 μL negative NHP, 72 μL of deionized water, and 155 μL Reagent A. The cell path length was 0.6 cm. The average $A_{340}$ (A=absorbance) values are found in Column C of Table 1. Duplicate rates were determined on the spiked and unspiked NHP and buffer similar to Example 1. The only changes from Example 1 for rate determinations were in the protocol timings. These changes are noted as follows. Reagent B and water were added in cycle 4. The analysis was finished at the end of cycle 15. Rates were determined using the 5 absorbance readings of cycles 11 through 15.

Averages of these rates are summarized in Table 2 in columns E through H.

In summary, the results of the study showed that all three of the anisic acids performed well as releasing agents with o-anisic acid showing somewhat better results than the meta and para isomers based on the smaller effect on the negative rate. The results showed that ANS had several effects on performance that were not desirable such as increased absorbance and discoloration of reagent when exposed to light. ANS has a significant contribution to background absorbance even at the relatively low level of 0.25 mM in Reagent A, thus limiting its use in assays, particularly those having an absorbance maximum.

The anisic acid isomers did not demonstrate these effects on absorbance or coloration with light exposure and all were effective in the release of MPA from NHP as seen by the equivalent or near equivalent rates of MPA in a non-protein matrix (buffer) and NHP. Without these agents, the MPA in buffer gave a higher rate (more apparent MPA) than the same concentration of MPA in NHP. The ortho isomer had the least effect on the negative rate. Furthermore, o-anisic acid was shown to quantitate MPA equivalently in a protein-free matrix and NHP.

TABLE 2

| RUN # | A Agent | B CONC. in Rgt A mM | C A 340 nm | D Δ A = agent-control Δ A 340 nm | E NHP with 0 μg/mL MPA Rate mA/min | F NHP with 10 μg/mL MPA Rate mA/min | G Buff with 0 μg/mL MPA Rate mA/min | H Buff with 10 μg/mL MPA Rate mA/min | I (H - G) Buff Rate Span mA/min | J (H - F) Buff-NHP Rate Diff. mA/min |
|---|---|---|---|---|---|---|---|---|---|---|
| 1 | NONE (control) | 0 | 0.457 | — | 161.0 | 240.5 | 159.4 | 250.8 | 91.4 | 10.3 |
|   | ANS | 0.25 | 0.779 | 0.322 | 158.2 | 274.2 | 156.0 | 276.2 | 120.2 | 2.0 |
| 2 | NONE (control) | 0 | 0.486 | — | 159.1 | 238.7 | 159.5 | 250.6 | 91.1 | 11.9 |
|   | o-AA | 12.5 | 0.490 | 0.004 | 169.5 | 276.9 | 168.2 | 277.5 | 109.3 | 0.6 |
|   | m-AA | 12.5 | 0.494 | 0.008 | 188.1 | 280.3 | 189.4 | 279.7 | 90.3 | −0.6 |
|   | p-AA | 12.5 | 0.494 | 0.008 | 182.7 | 280.4 | 182.3 | 278.3 | 96.0 | −2.1 |

The effectiveness of the releasing agent was determined by subtracting the spiked NHP rate from the spiked buffer rate (column H - column F). The closer this value was to zero, the better the releasing effect. Based on this criterion, all three of the anisic acid agents showed better MPA release when compared to the control, as seen by the results in column J. Thus, all three of the anisic acid agents diminished or eliminated the effect of NHP on MPA measurement, indicating total MPA was being measured.

Furthermore, it is seen that, although ANS can function as a releasing agent, ANS contributed detrimentally to background absorbance (column C and D) while the structural isomers of anisic acid have little or no effect on background absorbance. Also, Reagent A with ANS was found to become visibly discolored when exposed to light. This did not occur with the control or anisic acid reagents.

All four agents showed some non-detrimental or tolerable effects on either the negative rate and/or rate span as compared to control values. This indicated that the agents were having effects other than reducing the matrix effect of the NHP. ANS had the largest increase on rate span. The anisic acids had a marked increase in negative rate over the control whereas ANS had little or no effect. Although there were these effects on the negative rate relative to reagents without anisic acid, there did not appear to be an impact on assay performance because the negative rates for buffer and NHP were the same (see columns E and G). Very good assay sensitivity was achieved with o-anisic acid.

Example 3

Salicylic Acid as a Releasing Agent

In a separate study another agent, salicylic acid (2-hydroxybenzoic acid), was formulated into Reagent A at 12.5 and 25 mM. This agent reduced the Buffer rate span by 47% and increased the negative rate by 38% relative to the control without releasing agent. Rates were determined in a manner similar to that described in Example 2. Additionally, the 25 mM salicylic acid contributed 0.311 absorbance units above the control background at 340 nm. It is also noted that the Reagent A preparation of salicylic acid had a slight pink tinge. This visual color and the background absorbance at 340 nm may be due to the interaction of salicylic acid with the merest levels of ferric salts as reported in the Merck Index, eleventh edition, Merck & Co., Inc., Rahway, N.J., page 8300. Salicylic acid was eliminated from more extensive comparative studies due to these experimental results.

Example 4

Effect of o-Anisic Acid on MPA Rates in the Presence of Co-administered Drugs and Salicylic Acid In a separate study, the ability of o-anisic acid to eliminate the effect of salicylate on rates of MPA plasma spikes was compared. Two sets of antibody reagents (Reagent A) were prepared to the basic formulation described in Example 2 above. In one reagent, no releasing agent was added; in another reagent, o-anisic acid was added at 12.5 mM. A common Reagent B was prepared as described in Example 2.

Rates for four levels of MPA spikes into plasma and a plasma control were measured with each reagent set. A similar set of plasma spikes was prepared with plasma containing non-interfering co-administered drugs, and another set of plasma spikes was prepared containing non-interfering drugs plus salicylate. Concentrations of the non-interfering drugs in μg/mL were as follows: ampicillin, 36; cefaclor, 26; chloramphenicol, 64; trimethoprim, 2; albuterol, 7; isoproterenol, 18; metoprolol, 77; diltiazem, 28; nifedipine, 22; verapamil,12; fenoprofen, 16; indomethacin, 36; ketoconazole, 75; miconazole, 106; isoniazid, 120; 5-fluorouracil, 23; griseofulvin, 10; methotrexate, 2; diphenhydramine, 93; dl-ephedrine, 103; phenylephrine, 76; disopyramide, 52; procainamide, 64; metoclopramide, 5; niacin, 25; niacinamide, 47; acetaminophen, 87; and lidocaine, 43. Salicylate was present at 659 μg/mL.

Rates were determined as described in Example 2 above with the exception of the absorbance read window, which was extended to cycle 20 where the assay was ended. Rates were determined using the 10 consecutive absorbance readings of cycles 11 through 20. The results are summarized in Table 3.

TABLE 3

|  | Antibody Reagent Only | Antibody Reagent + o-Anisic Acid |
|---|---|---|
| MPA + MeOH* | | |
| 0 μg/mL | 149 | 161 |
| 0.5 μg/mL | 155 | 171 |
| 2.5 μg/mL | 181 | 210 |
| 5 μg/mL | 201 | 234 |
| 15 μg/mL | 240 | 264 |
| MPA + NI** | | |
| 0 μg/mL | 149 | 161 |
| 0.5 μg/mL | 158 | 173 |
| 2.5 μg/mL | 183 | 211 |
| 5 μg/mL | 204 | 234 |
| 15 μg/mL | 242 | 263 |
| MPA + NI + Salicylate** | | |
| 0 μg/mL | 149 | 161 |
| 0.5 μg/mL | 157 | 171 |
| 2.5 μg/mL | 190 | 211 |

TABLE 3-continued

|  | Antibody Reagent Only | Antibody Reagent + o-Anisic Acid |
|---|---|---|
| 5 μg/mL | 210 | 234 |
| 15 μg/mL | 250 | 263 |

*MeOH = plasma spiked with methanol as control for NI spike.
**NI = plasma contains spikes of non-interfering co-administered drugs in addition to MPA.

In summary, salicylate increased rates of MPA in normal human plasma in the absence of releasing agents, which could result in inaccurate quantitation of MPA in an assay. The presence of o-anisic acid as a releasing agent in the antibody reagent eliminated this potential problem in an assay for MPA.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art are intended to be within the scope of the following claims.

What is claimed is:

1. A method for releasing mycophenolic acid from a complex with endogenous proteins, said method comprising contacting a medium suspected of containing said complex with an effective amount of a compound of the formula:

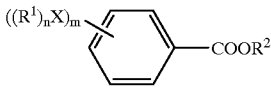

wherein $R^1$ is alkyl; $R^2$ is hydrogen or alkyl; X is O, S or N; n is 1 when X is O or S and n is 2 when X is N; and m is 1 or 2.

2. The method of claim 1 wherein X is O.

3. The method of claim 1 wherein said compound is methoxybenzoic acid.

4. The method of claim 1 wherein said compound is o-methoxybenzoic acid.

* * * * *